(12) United States Patent
Mian et al.

(10) Patent No.: US 9,134,185 B2
(45) Date of Patent: Sep. 15, 2015

(54) INFRARED-BASED VEHICLE COMPONENT IMAGING AND ANALYSIS

(71) Applicant: International Electronic Machines Corporation, Troy, NY (US)

(72) Inventors: Zahid F. Mian, Loudonville, NY (US); Ronald W. Gamache, East Greenbush, NY (US); Shankar B. Baliga, Irvine, CA (US)

(73) Assignee: International Electronic Machines Corp., Troy, NY (US)

( * ) Notice: Subject to any disclaimer, the term of this patent is extended or adjusted under 35 U.S.C. 154(b) by 29 days.

(21) Appl. No.: 13/895,275

(22) Filed: May 15, 2013

(65) Prior Publication Data

US 2013/0313433 A1 Nov. 28, 2013

Related U.S. Application Data

(60) Provisional application No. 61/688,843, filed on May 23, 2012.

(51) Int. Cl.
*G01J 5/20* (2006.01)
*G01K 13/08* (2006.01)
*G01J 1/42* (2006.01)
*G01J 5/02* (2006.01)
*G01J 5/06* (2006.01)
*G01J 5/00* (2006.01)

(52) U.S. Cl.
CPC ............... *G01K 13/08* (2013.01); *G01J 1/4228* (2013.01); *G01J 5/0022* (2013.01); *G01J 5/026* (2013.01); *G01J 5/061* (2013.01); *G01J 2005/0077* (2013.01)

(58) Field of Classification Search
CPC .......... G01J 5/20; G01J 5/0022; G01K 13/08
USPC ....................................... 250/338.4
See application file for complete search history.

(56) References Cited

U.S. PATENT DOCUMENTS 4,878,761 A * 11/1989 Duhrkoop .................... 374/124
5,331,311 A 7/1994 Doctor (Continued)

FOREIGN PATENT DOCUMENTS

EP 1600351 11/2005

OTHER PUBLICATIONS

MMR Technologies Inc., www.mmr-tech.com.*
Han Joong Sub, International Search Report and Written Opinion for PCT/US2013/041243, May 15, 2013, 13 pages.

(Continued)

*Primary Examiner* — David Porta
*Assistant Examiner* — Hugh H Maupin
(74) *Attorney, Agent, or Firm* — LaBatt, LLC

(57) ABSTRACT

An improved system for evaluating one or more components of a vehicle is provided. The system includes a set of imaging devices configured to acquire image data based on infrared emissions of at least one vehicle component of the vehicle as it moves through a field of view of at least one of the set of imaging devices. An imaging device in the set of imaging devices can include a linear array of photoconductor infrared detectors and a thermoelectric cooler for maintaining an operating temperature of the linear array of detectors at a target operating temperature. The infrared emissions can be within at least one of: the mid-wavelength infrared (MWIR) radiation spectrum or the long wavelength infrared (LWIR) radiation spectrum.

20 Claims, 8 Drawing Sheets

(56) References Cited

U.S. PATENT DOCUMENTS

| | | |
|---|---|---|
| 5,343,043 A | 8/1994 | Johnson |
| 5,677,533 A | 10/1997 | Yaktine et al. |
| 6,523,411 B1 | 2/2003 | Mian et al. |
| 7,312,454 B2 | 12/2007 | Safai et al. |
| 7,564,569 B2 | 7/2009 | Mian et al. |
| 8,006,559 B2 | 8/2011 | Mian et al. |
| 8,150,105 B2 | 4/2012 | Mian et al. |
| 8,335,606 B2 | 12/2012 | Mian et al. |
| 2003/0098412 A1 | 5/2003 | Gentala |
| 2009/0018721 A1 | 1/2009 | Mian et al. |
| 2010/0006761 A1 | 1/2010 | Johnson et al. |

OTHER PUBLICATIONS

Thermoelectric Cooling, CalSensors, 2008, 3 pages, CalSensors Inc.
IDA Compact integrated infrared detector assembly, CalSensors, 2 pages, CalSensors Inc.
AT2S Series—Two Stage (2.5W) TE Cooled SCD-13 Detectors, CalSensors, 2008, 1 page, CalSensors Inc.
Sensor System for Infrared Spectroscopy—Introduction, CalSensors, 58 pages.
Vergara et al., Polycrystalline lead selenide: the resurgence of an old infrared detector, Opto-electronics Review, 2007, pp. 110-117, vol. 15, No. 2.

* cited by examiner

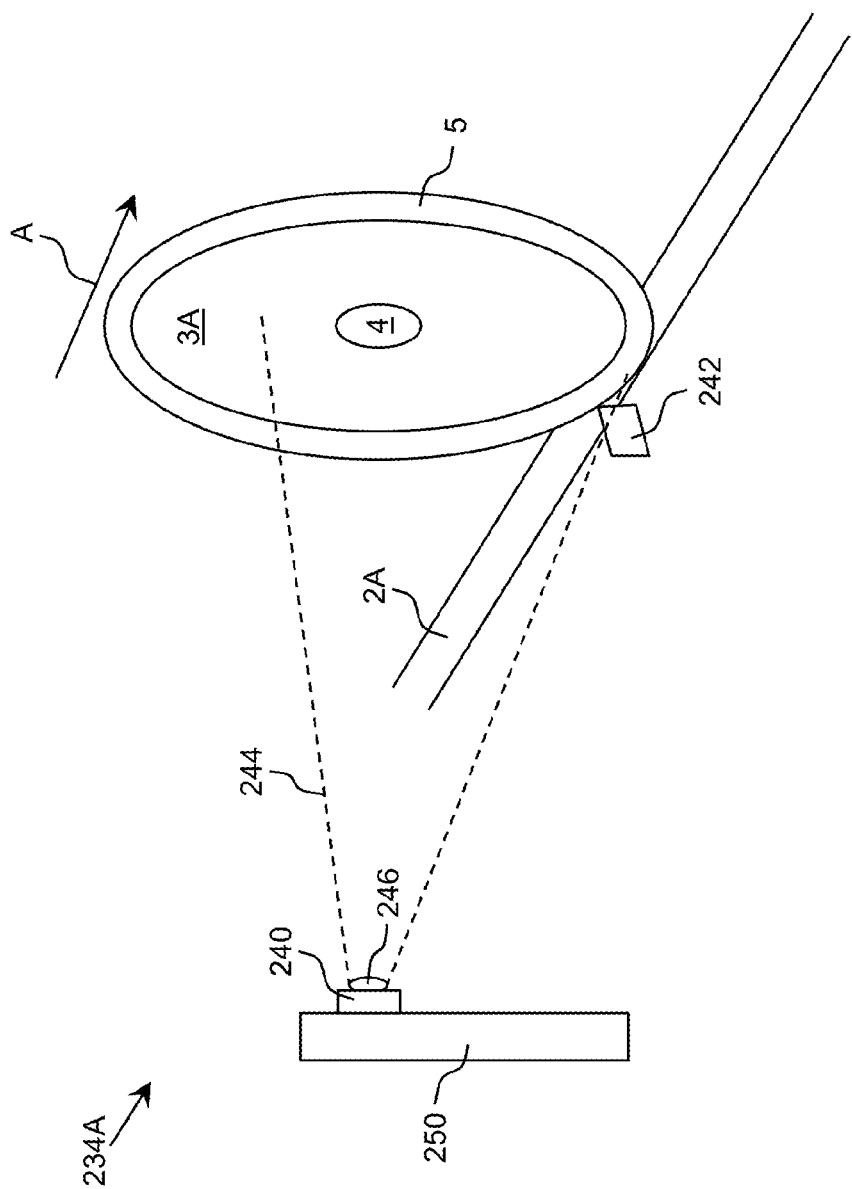

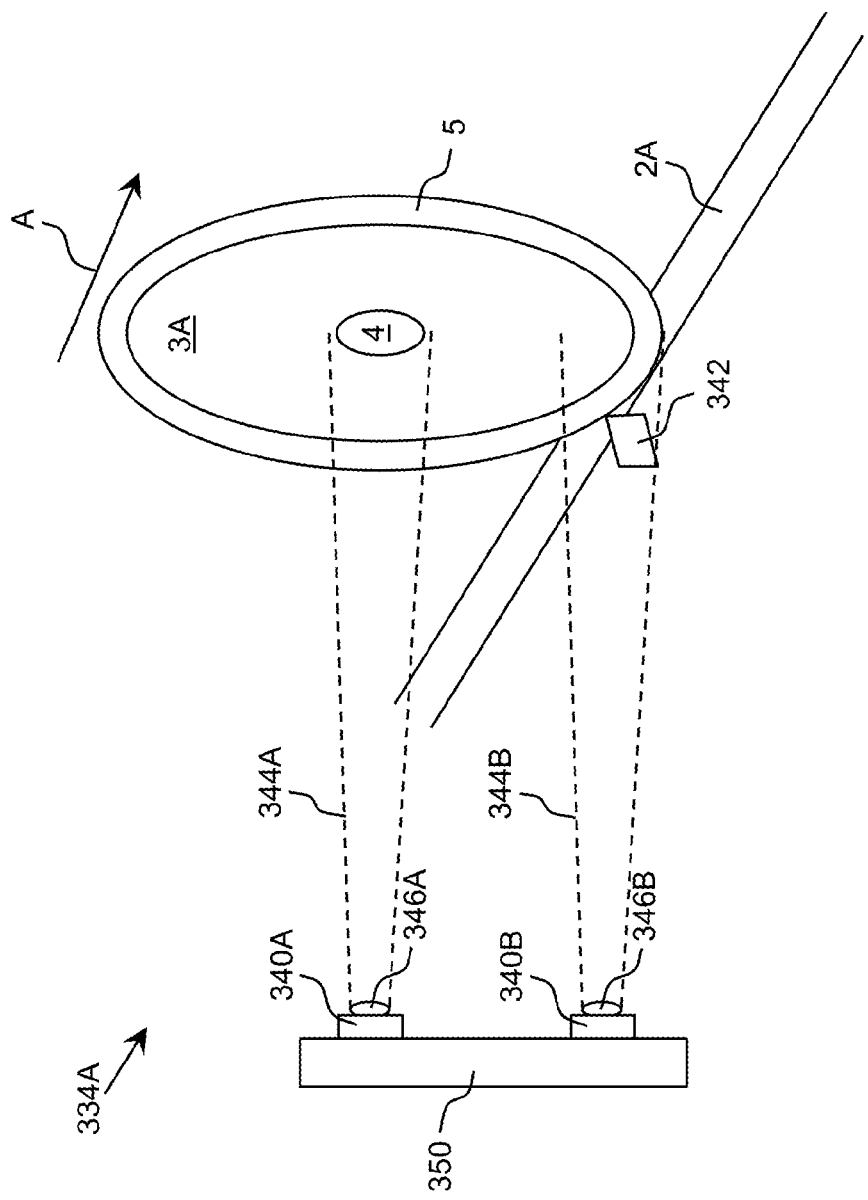

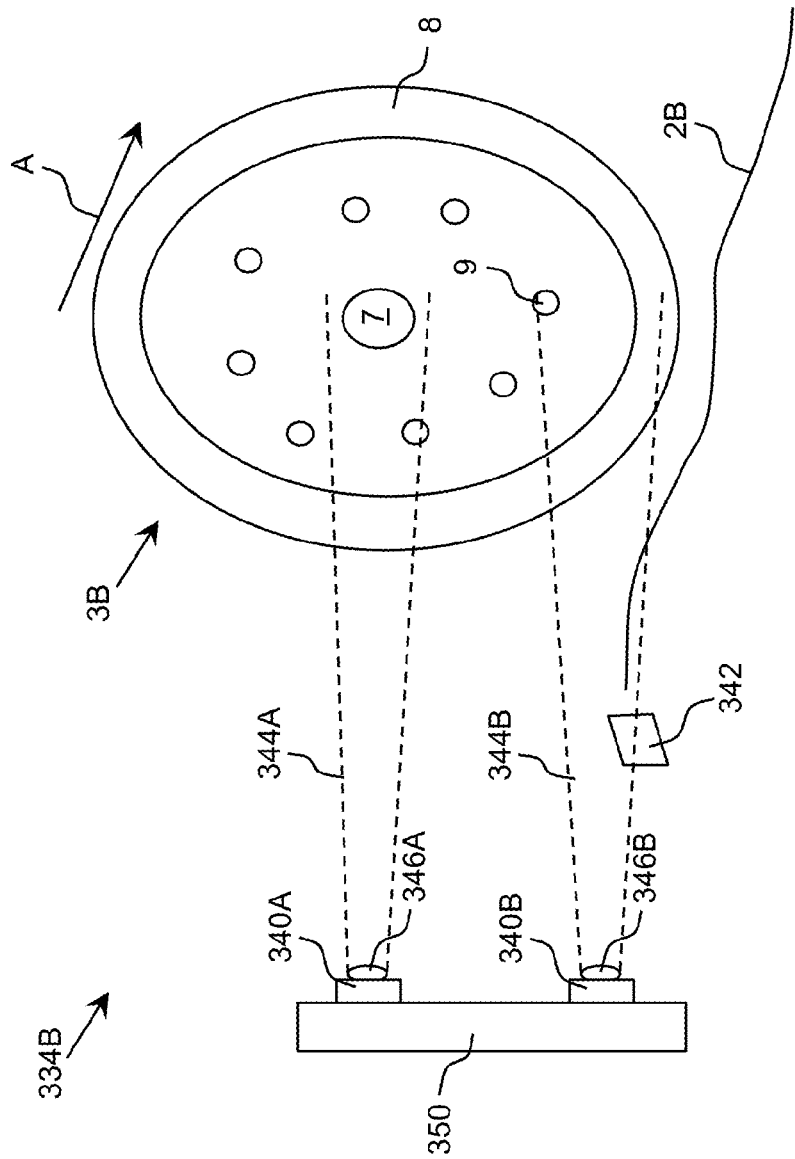

INFRARED-BASED VEHICLE COMPONENT IMAGING AND ANALYSIS

REFERENCE TO RELATED APPLICATIONS

The current application claims the benefit of U.S. Provisional Application No. 61/688,843, titled "Infrared array for high speed diagnostic imaging," which was filed on 23 May 2012, and which is hereby incorporated by reference.

TECHNICAL FIELD

The disclosure relates generally to wheeled vehicle monitoring, and more particularly, to a solution for evaluating a condition of a wheel, bearing, brake system, and/or the like, of a passing wheeled vehicle.

BACKGROUND ART

Effective detection of one or more flaws in vehicles, such as rolling stock components in the rail industry, or commercial trucks, is highly desirable. For example, detection of flaws or problems with the wheels, brake components (including drums, discs, etc.), electronic brake control systems, air conditioning units, transmission, driving motors, and/or the like, is desirable so that corrective action can be taken, e.g., to prevent a derailment, highway accident, further damage, fire, or the like.

Current detectors include detectors that attempt to detect bearing overheating (e.g., hot box detectors) and detectors that attempt to detect brake/wheel component overheating (e.g., hot wheel detectors). The rail industry has utilized hot-box detectors for over fifty years to detect overheating bearings and thereby prevent derailment. These thermal detectors are mounted on the rail or in close proximity to the rail to provide hot bearing and hot wheel data.

Measurements made with such single element detectors are subject to large errors due to variations in emissivity of bearing and wheel radiating surfaces. The infrared detectors typically used, such as thermoelectric, thermistor bolometer and pyroelectric detectors, also usually are limited to monitoring lower speed vehicles, e.g., vehicles typically traveling under one hundred fifty kilometers per hour. However, higher speed trains in use in Europe can travel as fast as four hundred fifty kilometers per hour.

Currently used thermal detectors monitor radiation in the long wave infrared (LWIR) region, e.g., having wavelengths between eight and fourteen microns. Thermal detectors are inherently slow as infrared absorption is followed by heating of the detector element mass. Heating of the detector element results in a physical property change, e.g., resistance change for the thermistor bolometer. An additional issue with existing rail mounted hot box detectors is microphonic noise generated by the pyroelectric detections in response to rail shock and vibration. Other difficulties with the use of conventional hot box and hot wheel detectors are the relative high cost of LWIR optics fabricated from germanium or special long wave infrared glasses, and the considerable motion induced blurring conspicuous with vehicles moving at higher operating speeds.

Previous approaches have proposed using arrays of pyroelectric detectors and thermopiles for hot wheel and hot bearing detection. For example, one approach includes a hot wheel detector that utilizes an eight element linear array of pyroelectric detectors. Another approach uses a vacuum packed micro thermopile (thermoelectric) array for wheel and bearing monitoring. However, these array detectors suffer from many of the drawbacks listed above regarding the use of conventional bolometer type thermal detectors in the LWIR region for hot wheel and hot bearing detection.

SUMMARY OF THE INVENTION

Aspects of the invention provide an improved system for evaluating one or more components of a vehicle. The system includes a set of imaging devices configured to acquire image data based on infrared emissions of at least one vehicle component of the vehicle as it moves through a field of view of at least one of the set of imaging devices. An imaging device in the set of imaging devices can include a linear array of photoconductor infrared detectors and a thermoelectric cooler for maintaining an operating temperature of the linear array of detectors at a target operating temperature, e.g., below ambient, for improved sensitivity. The infrared emissions can be within at least one of: the mid-wavelength infrared (MWIR) radiation spectrum or the long wavelength infrared (LWIR) radiation spectrum.

A first aspect of the invention provides a system comprising: an imaging component including a set of imaging devices configured to acquire image data based on infrared emissions of at least one vehicle component of a vehicle moving through a field of view of at least one of the set of imaging devices, wherein an imaging device in the set of imaging devices includes a lead selenide detector and a thermoelectric cooler for maintaining an operating temperature of the lead selenide detector at a target operating temperature; and a computer system for evaluating the at least one vehicle component based on the image data, wherein the evaluating includes: generating temperature measurement data based on the image data acquired by the set of imaging devices; and evaluating the at least one vehicle component using the temperature measurement data.

A second aspect of the invention provides a system comprising: an imaging component including a set of imaging devices configured to acquire image data based on infrared emissions of at least one vehicle component of a vehicle moving through a field of view of at least one of the set of imaging devices, wherein an imaging device in the set of imaging devices includes a detector and a thermoelectric cooler maintaining an operating temperature of the detector at a target operating temperature, and wherein the infrared emissions are within the mid-wavelength infrared (MWIR) radiation spectrum.

A third aspect of the invention provides a system comprising: an imaging component including a set of imaging devices configured to acquire image data based on infrared emissions of at least one vehicle component of a vehicle moving through a field of view of at least one of the set of imaging devices, wherein an imaging device in the set of imaging devices includes a linear array of photoconductor infrared detectors and a thermoelectric cooler for maintaining an operating temperature of the linear array of detectors at a target operating temperature, and wherein the infrared emissions are within at least one of: the mid-wavelength infrared (MWIR) radiation spectrum or the long wavelength infrared (LWIR) radiation spectrum.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIGS. 2A and 2B show partial configurations of illustrative imaging components according to embodiments.

FIGS. 3A and 3B show partial configurations of illustrative imaging components according to embodiments.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

The inventors recognize a further drawback with the use of commercially available thermal detectors. In particular, the performance of thermal detectors, such as thermistor bolometers and pyroelectrics, cannot be improved by adjusting their operating temperature. In contrast, the performance of another class of infrared detectors, known as photodetectors, can be improved by reducing the operating temperature, e.g., using one or more stages of thermoelectric cooling.

As indicated above, aspects of the invention provide an improved system for evaluating one or more components of a vehicle. The system includes a set of imaging devices configured to acquire image data based on infrared emissions of at least one vehicle component of the vehicle as it moves through a field of view of at least one of the set of imaging devices. An imaging device in the set of imaging devices can include a linear array of photoconductor infrared detectors and a thermoelectric cooler for maintaining an operating temperature of the linear array of detectors at a target operating temperature, e.g., below ambient, for improved sensitivity. The photoconductor infrared detectors can be formed of lead selenide, mercury cadmium telluride, and/or the like, which can provide fast response to enable accurate measurements of the fastest railcar wheels. The infrared emissions can be within at least one of: the mid-wavelength infrared (MWIR) radiation spectrum or the long wavelength infrared (LWIR) radiation spectrum. As used herein, unless otherwise noted, the term "set" means one or more (i.e., at least one) and the phrase "any solution" means any now known or later developed solution.

Figure 1:
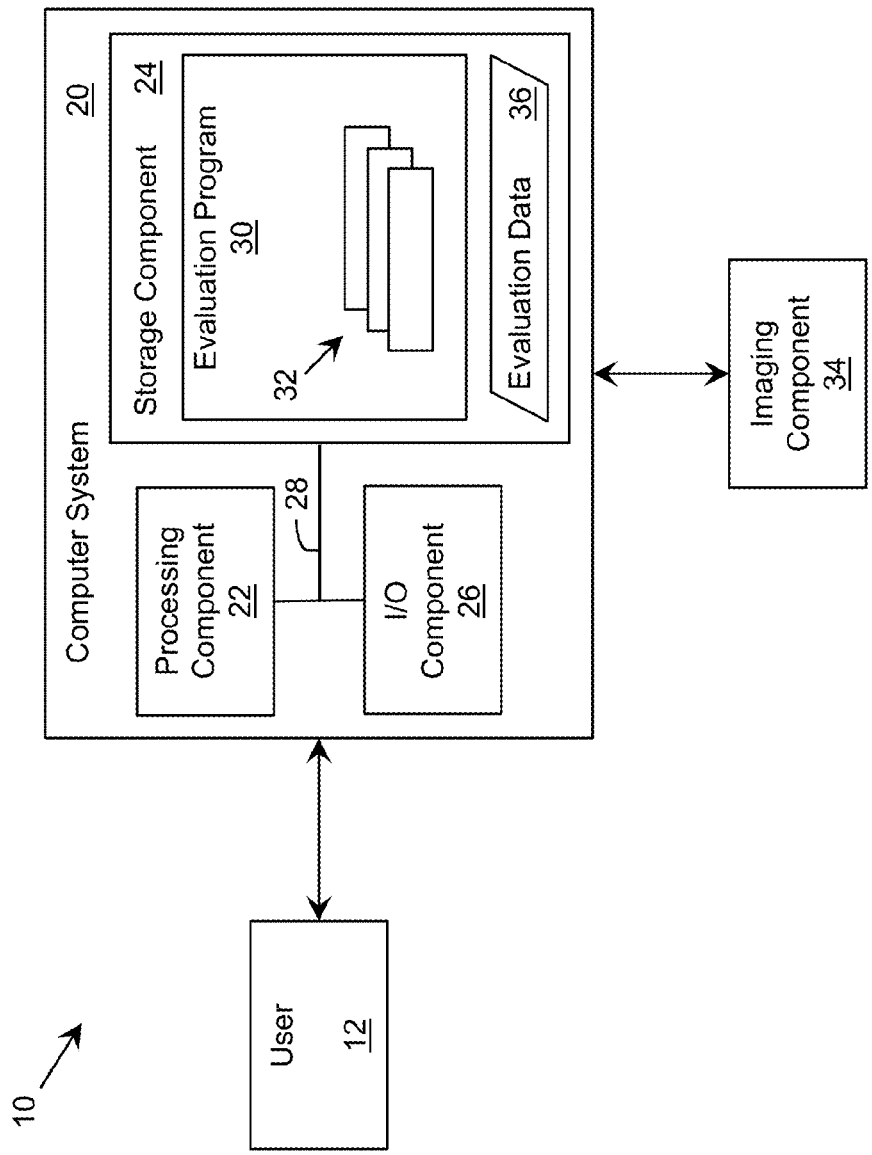
FIG. 1 shows an illustrative environment for evaluating a moving vehicle according to an embodiment.

Turning to the drawings, FIG. 1 shows an illustrative environment 10 for evaluating a moving vehicle according to an embodiment. To this extent, the environment 10 includes a computer system 20 that can perform a process described herein in order to evaluate the vehicle using image data acquired as the vehicle moves through a field of view of an imaging component 34. In particular, the computer system 20 is shown including an evaluation program 30, which makes the computer system 20 operable to evaluate the vehicle by performing a process described herein.

The computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, the processing component 22 executes program code, such as the evaluation program 30, which is at least partially fixed in storage component 24. While executing program code, the processing component 22 can process data, which can result in reading and/or writing transformed data from/to the storage component 24 and/or the I/O component 26 for further processing. The pathway 28 provides a communications link between each of the components in the computer system 20. The I/O component 26 can comprise one or more human I/O devices, which enable a human user 12 to interact with the computer system 20 and/or one or more communications devices to enable a system user 12 to communicate with the computer system 20 using any type of communications link. To this extent, the evaluation program 30 can manage a set of interfaces (e.g., graphical user interface(s), application program interface, and/or the like) that enable human and/or system users 12 to interact with the evaluation program 30. Furthermore, the evaluation program 30 can manage (e.g., store, retrieve, create, manipulate, organize, present, etc.) the data, such as evaluation data 36, using any solution.

In any event, the computer system 20 can comprise one or more general purpose computing articles of manufacture (e.g., computing devices) capable of executing program code, such as the evaluation program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the evaluation program 30 can be embodied as any combination of system software and/or application software.

Furthermore, the evaluation program 30 can be implemented using a set of modules 32. In this case, a module 32 can enable the computer system 20 to perform a set of tasks used by the evaluation program 30, and can be separately developed and/or implemented apart from other portions of the evaluation program 30. As used herein, the term "component" means any configuration of hardware, with or without software, which implements the functionality described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 20.

When the computer system 20 comprises multiple computing devices, each computing device can have only a portion of the evaluation program 30 fixed thereon (e.g., one or more modules 32). However, it is understood that the computer system 20 and the evaluation program 30 are only representative of various possible equivalent computer systems that may perform a process described herein. To this extent, in other embodiments, the functionality provided by the computer system 20 and the evaluation program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 20 includes multiple computing devices, the computing devices can communicate over any type of communications link. Furthermore, while performing a process described herein, the computer system 20 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols.

As discussed herein, the evaluation program 30 enables the computer system 20 to evaluate vehicle(s) using image data acquired by an imaging component 34. In an embodiment, the image data comprises image data acquired by a set of infrared imaging devices based on infrared radiation emitted from one or more components of each vehicle. In a more particular embodiment, the infrared radiation has a wavelength in the mid-wavelength infrared (MWIR) radiation spectrum, e.g., between approximately three and five micrometers (five to eight micrometer infrared radiation may be blocked by water vapor in the air). The computer system 20 can process the infrared image data to evaluate one or more components of a vehicle for the presence of one or more defects using any solution. Illustrative defects include hot or cold brakes, hot or cold wheels, hot bearings, and/or the like. In response to evaluating the presence of a defect, the computer system 20 can initiate any set of actions, including for example, activating a warning system for an operator of the vehicle, notifying a station to which the vehicle is traveling, activating a safety system (e.g., slowing the vehicle, removing the vehicle from a road, notifying other vehicles, and/or the like), identify the vehicle for further inspection, and/or the like.

The imaging component 34 can include one or more of any type of infrared-based imaging devices. Furthermore, the imaging component 34 can include one or more sub-components related to the imaging device(s). Illustrative sub-components include a set of wheel detectors, a set of speedometers, one or more devices for maintaining an atmosphere that enables effective operation of the imaging device(s) (e.g., shutters, air knives, cooling/heating elements, and/or the like), communications device(s), and/or the like. In an embodiment, the various components of the imaging component 34 communicate with and are controlled by the computer system 20. In another embodiment, the imaging component 34 includes a set of computing devices capable of controlling the various sub-components of the imaging component 34 and communicating with the computer system 20. In the latter case, the computing device(s) can be configured similar to the computer system 20.

In an embodiment, the imaging component 34 includes one or more sets of infrared photodetectors, which are capable of acquiring infrared-based image data at a target frame rate. For example, a set of infrared photodetectors can comprise a linear array of photodetectors sensitive to MWIR radiation. To this extent, an embodiment of the imaging component 34 can include one or more lead selenide (PbSe)-based photodetectors. Other possible MWIR photodetectors include lead sulfide (PbS) (e.g., when the vehicles are traveling sufficiently slow), mercury cadmium telluride, known as MCT or HgCdTe, and/or the like.

The target frame rate can be selected based on one or more attributes of the vehicle and the corresponding component(s) being imaged. In an embodiment, the vehicle is a rail vehicle, e.g., included in a train, and the component(s) being imaged are the bearings and/or wheels of the rail vehicle. In a more particular embodiment, the rail vehicle is included in a high speed train, which is capable of traveling at speeds of up to approximately four hundred fifty kilometers per hour. In another embodiment, the vehicle is a wheeled vehicle, such as a truck, and the component(s) being imaged are the brake rotors or brake drums (e.g., imaged through approximately two inch diameter openings in a wheel) and/or wheels of the truck. In a more particular embodiment, the vehicle is traveling at highway speeds, e.g., at speeds up to approximately one hundred twenty kilometers per hour. In either case, a target frame rate for evaluating the component(s) of the vehicle can be approximately two thousand frames per second.

In any event, the imaging device(s) included in the imaging component 34 can be permanently or temporarily placed adjacent to a path of travel for the vehicle(s) being imaged. The placement can be such that the desired component(s) of the vehicle will pass through the field of view of one or more of the imaging devices as the vehicle travels in a normal/expected path past the imaging device(s). The imaging component 34 can be configured to detect a presence of the vehicle and operate the imaging device(s) to acquire image data having a sufficient resolution to evaluate the component(s). In an embodiment, the resolution is approximately one quarter inch in the vertical and horizontal directions.

Figure 2B:
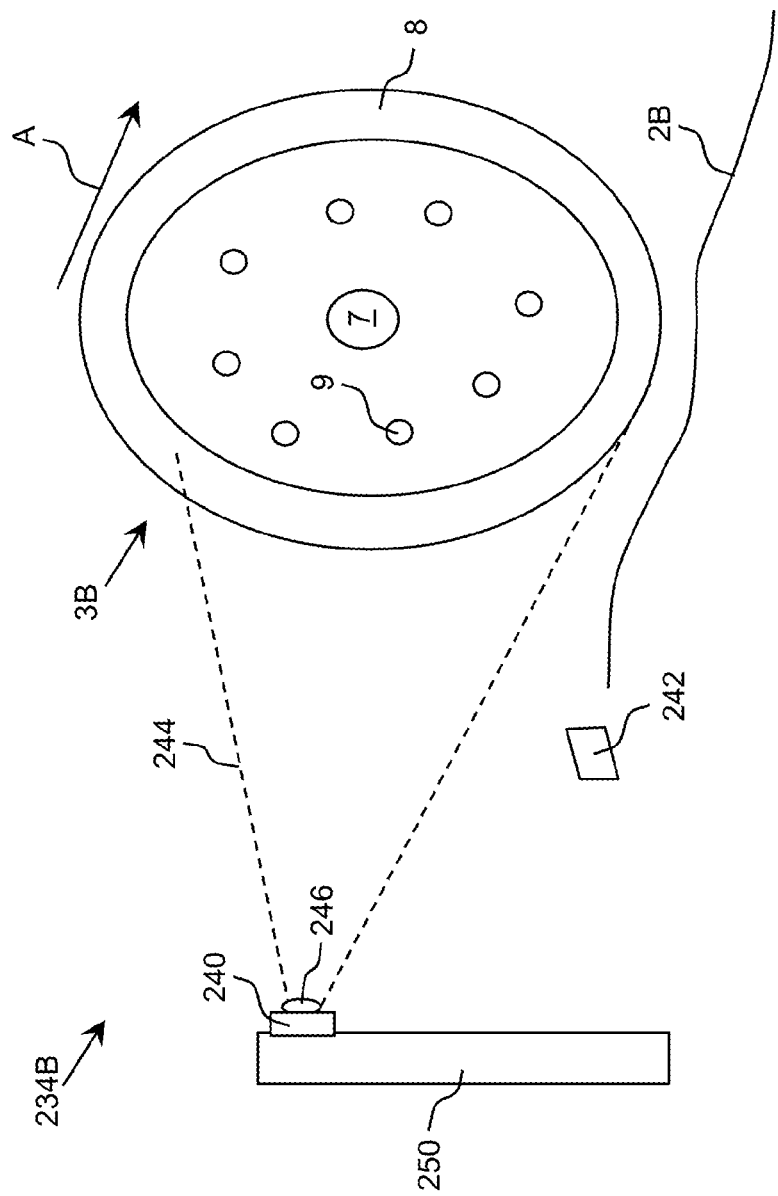

FIGS. 2A and 2B show partial configurations of illustrative imaging components 234A, 234B, respectively, according to embodiments. In FIG. 2A, an infrared imaging device 240 is mounted adjacent to a set of rails 2A, on which rail wheels 3A of a rail vehicle (not shown for clarity) travel. In FIG. 2B, an infrared imaging device 240 is mounted adjacent to a road 2B (e.g., a highway), on which the wheels 3B of a vehicle (not shown for clarity) travel. In an embodiment, the imaging component 234B is configured to evaluate the wheels 3B of trucks and other large vehicles traveling along a given road 2B.

As the wheel 3A, 3B travels, e.g., in a direction A, the wheel 3A, 3B can be detected by a wheel detector 242 included in the imaging component 234A, 234B. The wheel detector 242 can be any type of device capable of reliably detecting the presence of the corresponding type of wheel 3A, 3B. Additionally, the wheel detector 242 can be configured to determine one or more attributes of the wheel 3A, 3B, such as a speed at which the wheel 3A, 3B is traveling. In response to detecting a wheel 3A, 3B, the wheel detector 242 can send a signal, e.g., to the computer system 20 (FIG. 1) and/or the imaging device 240, which causes operation of the infrared imaging device 240 and/or one or more components related thereto to be initialized.

To this extent, the wheel detector 242 can be placed such that detection of the wheel 3A, 3B provides sufficient time to enable the infrared imaging device 240, and/or the component(s) related thereto, to be initialized for operation. Such a placement can be readily determined based on a maximum speed for the wheels 3A, 3B and an initialization time for the infrared imaging device 240 and/or the component(s) related thereto. Furthermore, it is understood that an imaging component 234A, 234B can include multiple wheel detectors 242, each of which can detect a wheel 3A, 3B as it passes a unique location to enable, for example, calculation of a speed of the wheel 3A, 3B (when the detectors are placed a known distance apart), detection of wheels 3A, 3B approaching from opposite sides of the infrared imaging device 240 (e.g., to handle vehicles traveling in different directions), detection of a wheel 3A, 3B immediately adjacent to a field of view of the infrared imaging device 240, and/or the like.

As shown in FIG. 2A, the rail wheel 3A includes a hub 4 and a rim 5. In general, the rail wheel 3A can have a diameter between approximately twenty-eight and forty-four inches, and the wheel hub 4 can be approximately fourteen to twenty-two inches above the rail 2A. As illustrated, the infrared imaging device 240 can be configured such that both the hub 4 and the rim 5 of the rail wheel 3A will pass through the vertical field of view 244 of the infrared imaging device 240 as the rail wheel 3A travels along the rail 2A.

As shown in FIG. 2B, the wheel 3B includes a hub 7 and a tire 8. Furthermore, the wheel 3B includes a plurality of openings 9. Each of the openings 9 can have a diameter of approximately two inches, through which a portion of a brake rotor of the corresponding vehicle is visible. However, it is understood that the configuration of the openings 9 on wheel 3B is only illustrative of various possible wheel opening configurations for a road vehicle. A typical truck wheel 3B can have a diameter between approximately forty and forty-four inches. As illustrated, the infrared imaging device 240 can be configured such that the hub 7, the tire 8, and one or more of the openings 9 of the wheel 3B will pass through the vertical field of view 244 of the infrared imaging device 240 as the wheel 3B travels along the road 2B.

In each imaging component 234A, 234B, the infrared imaging device 240 is shown mounted on an upright support 250. The support 250 can comprise any type of support, which is permanently or temporarily located adjacent to the rail 2A (FIG. 2A) or the edge of the road 2B (FIG. 2B). In either case, the support 250 can provide sufficient stability during the passing of a vehicle to enable the infrared imaging device 240 to capture infrared data having sufficient clarity and resolution for evaluating the wheel 3A, 3B and/or other components of the vehicle. In an embodiment, the infrared imaging device 240 is mounted pointing slightly down, e.g., at a downward angle of approximately five degrees, to provide protection from rain, snow, debris buildup, and/or the like.

The upright support 250 can be located a predetermined distance from the rail 2A (FIG. 2A) or the edge of the road 2B (FIG. 2B). The infrared imaging device 240 can include a lens system 246, which provides the desired vertical field of view 244. The predetermined distance and height at which the infrared imaging device 240 is mounted, can be selected based on the vertical field of view 244 and the corresponding dimensions of the wheel 3A, 3B using any solution. In an embodiment, the predetermined distance is approximately four feet, the height is approximately eighteen inches above the surface on which the wheel 3A, 3B travels (e.g., the rail 2A or the road 2B), and the vertical field of view 244 is approximately thirty degrees. When implemented on the side of a road 2B, it is understood that the distance between the wheel 3B and the infrared imaging device 240 can vary, e.g., by approximately +/− two feet.

In an embodiment, the infrared imaging device 240 comprises a linear array of photoconductor infrared detectors for acquiring MWIR image data. A photoconductor infrared detector is a class of photodetectors that undergo a large resistance change on illumination with radiation. Another class of photodetectors is photovoltaic, which generate a voltage in response to illumination. In a more particular embodiment, the photoconductor infrared detectors are formed of lead selenide (PbSe). In an illustrative embodiment, the linear array can comprise a sixty-four by one linear array of photoconductive infrared detectors. Regardless, a horizontal field angle for the linear array can be approximately 0.2 to 0.3 degrees, which can be selected based upon the lens system 246 and a desired array pixel size (e.g., approximately one quarter inch squares in an embodiment). However, it is understood that the linear array size and pixel size are only illustrative. To this extent, various other linear array sizes (e.g., 256×1 or greater) and/or pixel sizes can be utilized.

As a wheel 3A, 3B passes through the field of view 244 of the imaging device 240, the imaging device can acquire multiple frames of image data corresponding to MWIR radiation emitted by the imaged components of the wheel 3A, 3B and/or corresponding vehicle. When the infrared imaging device 240 comprises a linear array, each frame corresponds to a vertical slice of the wheel 3A, 3B. As described herein, operation of the infrared imaging device 240 can be synchronized with the passage of a wheel 3A, 3B using, for example, data provided by the wheel detector 242.

The imaging device 240 can provide the acquired infrared image data, or data corresponding thereto, for processing by the computer system 20 (FIG. 1) using any solution. When the imaging device 240 comprises a linear array, each frame will represent a different portion (e.g., slice) of the wheel 3A, 3B due to the motion of the wheel 3A, 3B between the capture of each frame. The computer system 20 can assemble a series of frames into a two-dimensional image of the wheel 3A, 3B. Each line portion of the resulting two-dimensional image is temporally shifted based upon the frame rate of the imaging device 240. The computer system 20 can store the infrared image data, the two-dimensional image, and/or the like, as evaluation data 36 corresponding to the wheel 3A, 3B.

The computer system 20 can process the infrared image data to evaluate one or more attributes of the wheel 3A, 3B and/or another component of the vehicle related to the wheel. For example, the computer system 20 can process each frame/two-dimensional image to determine a corresponding temperature distribution of the imaged wheel 3A, 3B and/or other components of the vehicle present in the image data. The temperatures calculated by the computer system 20 based on MWIR-based image data should not be influenced by variations in the distance between the wheel (particularly the wheel 3B) and the infrared imaging device 240. As a result, it is not critical to know an exact distance between the infrared imaging device 240 and the wheel 3A, 3B. The two-dimensional image of the wheel 3A, 3B generated by the computer system 20 can be elliptical. The size and shape of the wheel 3A, 3B in the image can depend on the distance between the infrared imaging device 240 and the wheel 3A, 3B, the frame rate of the infrared imaging device 240, the speed of the wheel 3A, 3B, and/or the like. In an embodiment, the computer system 20 can implement one or more feature extraction algorithms to calculate a distance to the wheel 3A, 3B, if desired, to calculate a speed of the wheel 3A, 3B from the elliptical shape, and/or the like.

Regardless, when a rail wheel 3A is imaged, the computer system 20 can process the infrared image data to obtain temperature measurement data corresponding to the hub 4, the rim 5, and/or the like, using any solution. The computer system 20 can use the temperature measurement data for the rail wheel 3A to evaluate a condition of wheel bearings, brakes, the wheel 3A, and/or the like, using any solution. When a road wheel 3B is imaged, the computer system 20 can process the infrared image data to obtain temperature measurement data corresponding to the hub 7, tire 8, a portion of a brake rotor (e.g., visible through the openings 9), and/or the like, using any solution. The computer system 20 can use the temperature measurement data for the road wheel 3B to evaluate a condition of wheel bearings, brakes, tires, and/or the like, using any solution. For example, the computer system 20 can compare the temperature measurement data to determine whether the temperatures are within an expected range of temperatures (e.g., relative to a running average), exceed or are below a maximum/minimum allowable temperature, are correlated with the temperature measurements acquired for other components (e.g., other wheels of the same vehicle, other rail cars on the same train, and/or the like), and/or the like.

It is understood that various alternative configurations of the imaging components 234A, 234B are possible. For example, more or less of each wheel 3A, 3B can be imaged, multiple infrared imaging devices 240 can be included, other components of the vehicle can be imaged, and/or the like. Similarly, it is understood that each imaging component 234A, 234B can include a similarly configured infrared imaging device 240 on an opposing side of the rail(s) 3A or road 3B to image wheels 3A, 3B on the opposing side of the vehicle.

FIGS. 3A and 3B show partial configurations of illustrative imaging components 334A, 334B according to embodiments. Similar to the imaging components 234A, 234B shown in FIGS. 2A and 2B, the imaging components 334A, 334B include a set of infrared imaging devices 340A, 340B, which are mounted on an upright support 350 located adjacent to a set of rails 2A and a road 2B, respectively. Additionally, the imaging components 334A, 334B are shown including a wheel detector 342, which can detect a passing wheel 3A, 3B, and initiate operation of the infrared imaging devices 340A, 340B, synchronize operation of the imaging devices 340A, 340B with the wheel 3A, 3B moving in the direction A, and/or the like, as described herein.

In these embodiments, the imaging components 334A, 334B include two infrared imaging devices 340A, 340B. Each infrared imaging device 340A, 340B can be configured similarly to the infrared imaging device 240 described in conjunction with FIGS. 2A and 2B. For example, each infrared imaging device 340A, 340B can comprise a linear array of photoconductor infrared detectors for acquiring MWIR image data. However, each infrared imaging device 340A, 340B can have a narrower vertical field of view 344A, 344B, respectively, than that of the infrared imaging device 240. To this extent, in order to obtain the same resolution as the infrared imaging device 240, the linear array for each infrared imaging device 340A, 340B can be smaller than the linear array of the infrared imaging device 240. The use of multiple smaller linear photoconductive arrays for concurrent imaging of different sections of interest of the wheel 3A, 3B can provide a solution having: a lower cost (e.g., a photoconductive array can be expensive as the number of elements are increased); a more detailed and higher resolution image data for wheel 3A, 3B sections of interest (e.g., hot bearings and hot rims); less image data to process; and/or the like.

Each infrared imaging device 340A, 340B can be separately configured based on a target area to be imaged. For example, the infrared imaging device 340A can have a field of view that is at least two times larger than the field of view of the infrared imaging device 340B. Similarly, the infrared imaging device 340A can comprise a linear array of photoconductor infrared detectors that is at least two times larger than the linear array of photoconductor infrared detectors for the infrared imaging device 340B. In an embodiment, the infrared imaging device 340A comprises a thirty-two by one linear array of photoconductor infrared detectors formed of PbSe. A corresponding lens system 346A can provide a vertical field of view of approximately seventeen degrees. The infrared imaging device 340A can be mounted approximately eighteen (in FIG. 3A) or twenty (in FIG. 3B) inches above the surface on which the wheel 3A, 3B is traveling pointing slightly down. In this configuration, the infrared imaging device 340A can acquire infrared image data corresponding to the hub 4, 7 of the wheel 3A, 3B, respectively, which can enable detection of a hot bearing.

In an embodiment, the infrared imaging device 340B comprises an eight by one linear array of photoconductor infrared detectors formed of PbSe. A corresponding lens system 346B can provide a vertical field of view of approximately 3.6 degrees. The infrared imaging device 340B can be mounted approximately three inches above the surface on which the wheel 3A, 3B is traveling pointing slightly down. In this configuration, the infrared imaging device 340B can acquire infrared image data corresponding to the rim 5 of the wheel 3A, or the rim (which can include one or more of the openings 9) and/or the tire 8 of the wheel 3B, respectively, which can enable detection of a hot rim, a hot tire, hot brakes, and/or the like.

Figure 4:
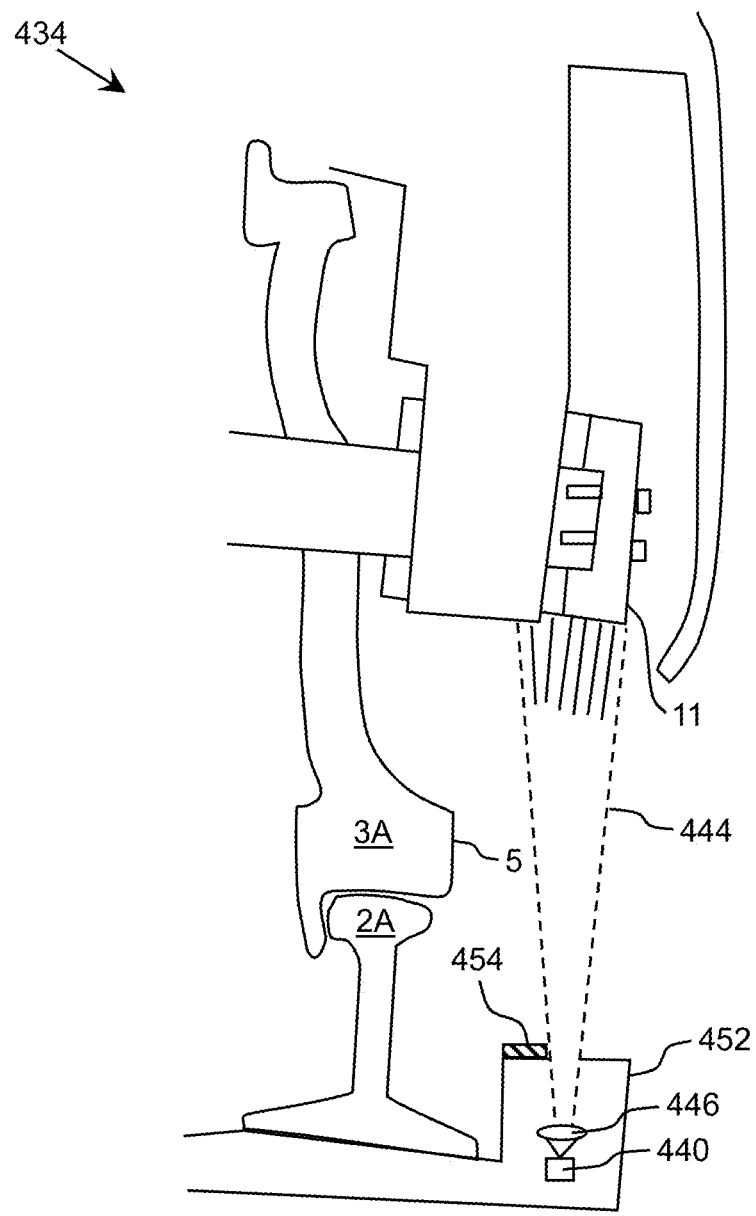
FIG. 4 shows a partial configuration of an illustrative imaging component according to an embodiment.

In some applications, such as transit rail service, the wheel hub 4, 7, may be covered by other hardware, and therefore not viewable or imageable from the side of the rail/road. In this case, one or more infrared imaging devices can be mounted in an alternative location, which enables the capture of infrared image data for the wheel hub 4, 7. For example, FIG. 4 shows a partial configuration of an illustrative imaging component 434 according to an embodiment. In this case, an infrared imaging device 440 and corresponding lens system 446 is mounted in a housing 452 connected to the rail 2A and located below a top surface of the rail 2A. The infrared imaging device 440 is shown having a field of view 444 which is substantially vertical and enables acquiring infrared image data for a bearing 11 of a wheel 3A. However, it is understood that this is only illustrative of various possible configurations. For example, in an embodiment, the infrared imaging device 440 can be configured to acquire infrared image data for a rim 5 of the wheel 3A.

The housing 452 can be mounted to the rail 2A using any solution. The housing 452 can include a movable shutter 454, which covers an opening when the infrared imaging device 440 is not in use to protect the interior from rain, snow, ice, and/or the like. The movable shutter 454 can be moved away from the opening when the infrared imaging device 440 is in use, e.g., in response to a wheel being detected by a wheel detector. Additionally, the housing 452 can include one or more components, such as rotating mirrors, air knives, and/or the like, to protect the infrared imaging device 440 and lens system 446 from blowing dirt and other contaminants while the movable shutter 454 is open.

The infrared imaging device 440 can be configured similar to the infrared imaging devices described herein. In an embodiment, the infrared imaging device 440 comprises a single photoconductor infrared detector or a linear array of photoconductor infrared detectors which can be formed of, for example, PbSe. Use of photoconductor infrared detector(s) in this case, where the infrared imaging device 440 is subjected to vibrations induced by a passing train, eliminates the microphonic noise, which causes false alarms with pyroelectric detectors typically used in the prior art.

The use of a linear array of photoconductor infrared detectors described herein enables high speed capture (approximately two thousand frames per second) of the radiant energy emitted by various components being imaged. Such a high speed capture can be required to perform certain analysis of one or more components of a vehicle traveling at a normal operating speed. For example, as described herein, for a road-side embodiment, the road vehicle (e.g., a truck) can be traveling at a highway speed (e.g., approximately seventy miles per hour or faster). In this case, in order to analyze the radiant energy emitted by the brake rotor, which is imaged through the openings 9 (FIGS. 2B and 3B), a frame rate of approximately two thousand frames per second may be necessary. Similarly, for a rail vehicle traveling at high speeds (e.g., up to approximately four hundred fifty kilometers per hour), a frame rate of approximately two thousand frames per second may be necessary to analyze the hub 4 and/or rim 5 of each rail wheel 3A. Since the features of interest on the rail wheel 3A are continuous (e.g., are fully visible), the rail vehicle can be traveling at a much higher speed than the road vehicle.

As described herein, an infrared imaging device can include one or more photoconductor infrared detectors made of lead selenide. Photoconductive lead selenide has a relatively fast response, e.g., a typical rise time of approximately ten microseconds, and is sensitive to MWIR radiation having wavelengths between approximately 1.5 and 5.2 micrometers.

A commonly used and appropriate figure of merit for infrared detectors is $D^*$, where $D^*$ is measured in $cmHz^{1/2} Watt^{-1}$. $D^*$ is a measure of the signal to noise provided by an infrared detector after normalizing for the detector element area and the measurement bandwidth, thereby enabling different detectors to be compared equitably. A value of $D^*$ in a range of $1E+10$ $cmHz^{1/2} Watt^{-1}$ and higher can provide meaningful measurement of radiant energy for many applications, enabling surface temperatures and small temperature differences of radiating surfaces to be resolved via infrared measurements. Lead selenide-based detectors provide a $D^*$ in the range of $1E+10$ $cmHz^{1/2} Watt^{-1}$ at ambient temperature ($25°$ C.) operation. Performance of a lead selenide-based detector (and detector arrays) can be improved by operating the detector(s) at lower temperatures. Such an improvement may be required for MWIR measurements for objects at or near ambient temperatures, e.g., due to a relatively small amount of MWIR energy emitted by such objects.

Figure 5:
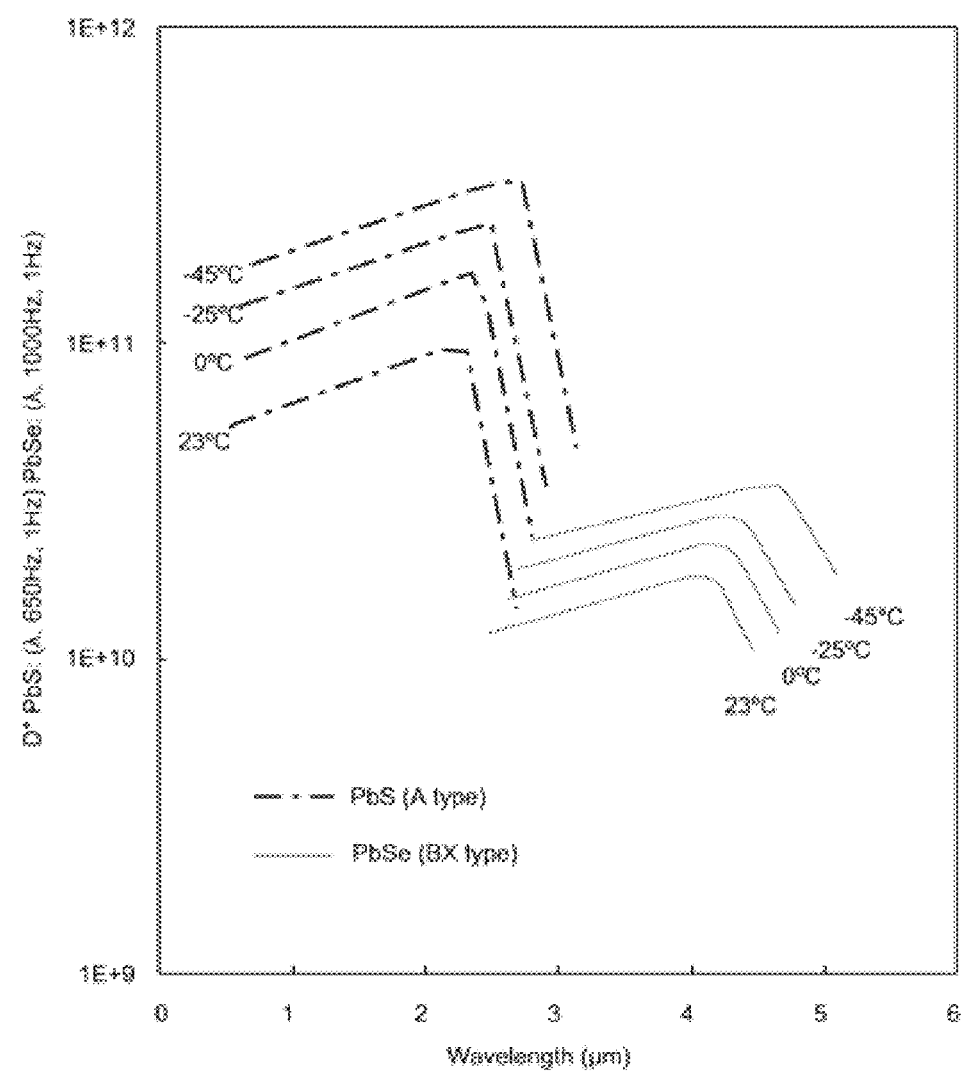
FIG. 5 shows D* as a function of wavelength for different operating temperatures of two types of photoconductive infrared detectors.

FIG. 5 shows $D^*$ as a function of wavelength for different operating temperatures of two types of photoconductive infrared detectors. In particular, the $D^*$ for lead selenide (PbSe) and lead sulfide (PbS) detectors are shown for operating temperatures of −45, −25, 0, and 23 degrees Celsius. An improvement in $D^*$ by a factor of two to three can be obtained by operating the detector or detector array at reduced temperatures, e.g., 0° C. or below. While the PbS detectors have a higher $D^*$ than the PbSe detectors, these detectors are much slower, e.g., with rise times in the hundreds of microseconds. As a result, use of a PbS detector can be limited to applications in which lower frame rates are acceptable (e.g., slower speeds of the vehicles). A mercury cadmium telluride (MCT)-based detector can have sufficient sensitivity ($D^*$) and operate sufficiently fast to provide high speed imaging. These detectors can be operated in either a photovoltaic or a photoconductive mode. Use of an MCT-based detector can include maintaining a target operating temperature using a cryogenic cooling solution, e.g., an operating temperature of approximately 77 degrees Kelvin maintained using a liquid nitrogen cooling solution, or the like.

Figure 6:
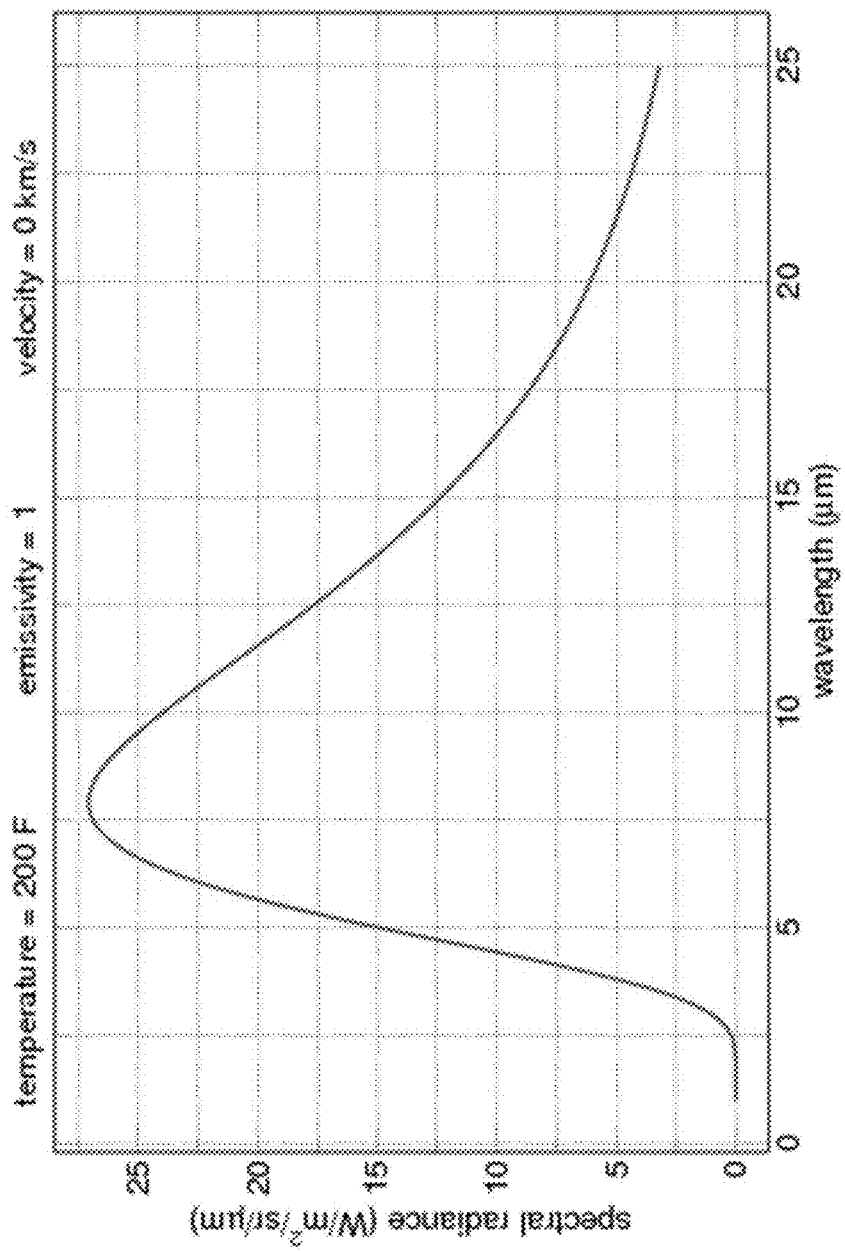
FIG. 6 shows spectral radiance emitted by a blackbody at a temperature of two hundred degrees Fahrenheit.

FIG. 6 shows spectral radiance emitted by a blackbody at a temperature of two hundred degrees Fahrenheit. Calculations show that less than five percent of the energy is emitted in the infrared region between one to five micrometers wavelength. As illustrated, most of the energy radiated by such warm (as opposed to hot) objects is in the long wavelength infrared (LWIR) region. To this extent, it is desirable to have a relatively high signal to noise ratio for an MWIR imaging device in order to accurately measure warm (e.g., a temperature less than approximately two hundred degrees F.) wheel/vehicle components.

In an embodiment, an infrared imaging device described herein maintains an operating environment, which enables the detector element(s) to acquire data having a signal to noise ratio sufficient for a given application. In a more specific embodiment, the infrared imaging device can maintain the detector element(s) at a target operating temperature, which can be below ambient. For example, the infrared imaging device can include thermoelectric coolers, which are mounted inside the detector package to reduce the operating temperature of the infrared detector(s). In an embodiment, the thermoelectric cooler is a single stage thermoelectric cooler, which is capable of reducing the operating temperature to approximately −25° C. for ambient temperatures of 25° C. with a power consumption of 1 to 2 Watts. A lower operating temperature can be achieved using two or three stage thermoelectric coolers, which have a proportionally higher power consumption. In an embodiment, an infrared imaging device comprises a self-contained device capable of maintaining a target operating temperature. In another embodiment, the computer system 20 (FIG. 1) is configured to operate a set of thermoelectric coolers to maintain the target operating temperature. In either case, the target operating temperature can be precisely controlled, e.g., within +/−0.01° C. of the target operating temperature.

A linear array of PbSe-based detector elements with operating temperatures of, for example, −4° C., is currently available. A second stage of cooling can be added between the cooled array and an external heat radiator to further reduce the temperature. A signal to noise improvement of approximately 3%/° C. is estimated for further temperature reduction, e.g., down to approximately −80° C. While use of cooling elements is described herein, it is understood that an infrared imaging device can include one or more heating elements, which can be utilized to maintain the target operating temperature depending on the operating environment and/or the target operating temperature. In an embodiment, the set of thermoelectric coolers is operated using a reverse current to provide heating. In another embodiment, an infrared imaging device described herein can include an additional heating element, such as a resistive heater, which can be utilized, for example, in operating environments with temperatures below −55° C.

In addition to improvements in sensitivity, the stabilization of the detector temperature results in reduced noise and drift. Hence, temperature stabilization via use of thermoelectric coolers can be beneficial even if temperature reduction is not required for sensitivity enhancement. Furthermore, as illustrated in FIG. 5, the wavelength response of a PbSe or PbS detector shifts to longer wavelengths at the reduced operating temperatures. To this extent, cooling of a detector described herein can provide an additional improvement in performance for measurements conducted on warm objects. In particular, as shown in FIGS. 5 and 6, significantly more infrared energy will detected from objects at 200° F. as the detector response shifts to longer wavelengths with cooling below 23° C. The steep increase in spectral radiance emitted by warm objects in the wavelength region around five microns (FIG. 6) overlaps with the increase in the long wavelength detection edge (FIG. 5) of the cooled PbSe detectors.

While shown and described herein as a method and system for evaluating one or more components of a vehicle, it is understood that aspects of the invention further provide various alternative embodiments. For example, in one embodiment, the invention provides a computer program fixed in at least one computer-readable medium, which when executed, enables a computer system to evaluate component(s) of the vehicle. To this extent, the computer-readable medium includes program code, such as the evaluation program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the invention provides a method of providing a copy of program code, such as the evaluation program 30 (FIG. 1), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for evaluating component(s) of a vehicle. In this case, the generating can include configuring a computer system, such as the computer system 20 (FIG. 1), to implement the method of evaluating component(s) of the vehicle. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
an imaging component including a set of imaging devices configured to acquire image data based on infrared emissions of at least one vehicle component of a vehicle moving at any speed in a range of speeds including a maximum main line operating speed of the vehicle through a field of view of at least one of the set of imaging devices, wherein an imaging device in the set of imaging devices includes a high speed infrared detector and a temperature element for maintaining an operating temperature of the high speed infrared detector at a target operating temperature, wherein the high speed infrared detector is a lead selenide detector, wherein the temperature element comprises a multi-stage cooler configured to maintain the target operating temperature between −80 degrees Celsius and −25 degrees Celsius, and wherein the infrared emissions are within the mid-wavelength infrared (MWIR) radiation spectrum; and
a computer system for evaluating the at least one vehicle component based on the image data, wherein the evaluating includes:
generating temperature measurement data based on the image data acquired by the set of imaging devices; and
evaluating the at least one vehicle component using the temperature measurement data.

2. The system of claim 1, wherein the high speed infrared detector comprises a linear array of photoconductor infrared detectors.

3. The system of claim 1, wherein an imaging device in the set of imaging devices is capable of acquiring infrared image data at a rate of at least approximately two thousand frames per second.

4. The system of claim 1, wherein the set of imaging devices includes:
a first imaging device configured to acquire image data for a central region of a wheel of the moving vehicle; and
a second imaging device configured to acquire image data for an outer region of the wheel of the moving vehicle, wherein the first and second imaging devices acquire image data for distinct regions of the wheel.

5. The system of claim 1, wherein the set of imaging devices are located approximately four feet from a rail on which the vehicle is moving.

6. The system of claim 1, wherein the set of imaging devices are located adjacent to a road on which the vehicle is moving, and wherein the vehicle can be moving up to at least approximately seventy miles per hour while the set of imaging devices acquire the image data.

7. The system of claim 1, wherein a second imaging device in the set of imaging devices includes a second high speed infrared detector, and wherein the infrared emissions are further within the long wavelength infrared (LWIR) radiation spectrum.

8. A system comprising:
an imaging component including a set of imaging devices configured to acquire image data based on infrared emissions of at least one vehicle component of a vehicle moving at any speed in a range of speeds including a maximum main line operating speed of the vehicle through a field of view of at least one of the set of imaging devices, wherein an imaging device in the set of imaging devices includes a high speed lead selenide infrared detector and a temperature element maintaining an operating temperature of the high speed infrared detector at a target operating temperature, wherein the target operating temperature for the lead selenide infrared detector is between −80 degrees Celsius and −25 degrees Celsius, and wherein the infrared emissions are within the mid-wavelength infrared (MWIR) radiation spectrum.

9. The system of claim 8, wherein the temperature element comprises a multi-stage cooler configured to precisely control the operating temperature.

10. The system of claim 8, wherein an imaging device in the set of imaging devices is capable of acquiring infrared image data at a rate of at least approximately two thousand frames per second.

11. The system of claim 8, further comprising a computer system for evaluating the at least one vehicle component based on the image data, wherein the evaluating includes:
generating temperature measurement data based on the image data acquired by the set of imaging devices; and evaluating the at least one vehicle component using the temperature measurement data.

12. The system of claim 8, wherein an imaging device in the set of imaging device comprises a linear array of photoconductor infrared detectors.

13. The system of claim 12, wherein the set of imaging devices include:
a first imaging device configured to acquire image data for a central region of a wheel of the moving vehicle, wherein the first imaging device comprises a linear array of photoconductor infrared detectors of a first size; and
a second imaging device configured to acquire image data for an outer region of the wheel of the moving vehicle, wherein the second imaging device comprises a linear array of photoconductor infrared detectors of a second size, wherein the first size is at least twice as large as the second size.

14. A system comprising:
an imaging component including a plurality of imaging devices configured to acquire image data based on infrared emissions of at least one vehicle component of a vehicle moving at any speed in a range of speeds including a maximum main line operating speed of the vehicle through a field of view of at least one of the plurality of imaging devices, wherein the set plurality of imaging devices includes at least two high speed linear arrays of photoconductor infrared detectors of different sizes and a temperature element for maintaining an operating temperature of the at least two linear arrays of detectors at a target operating temperature between −80 degrees Celsius and −25 degrees Celsius, and wherein the infrared emissions are within at least one of: the mid-wavelength infrared (MWIR) radiation spectrum or the long wavelength infrared (LWIR) radiation spectrum.

15. The system of claim 14, wherein the at least two linear arrays of detectors includes at least one of: lead selenide photoconductor infrared detectors or mercury cadmium telluride photoconductor infrared detectors.

16. The system of claim 14, wherein the temperature element comprises a multi-stage cooler configured to precisely control the target operating temperature.

17. The system of claim 14, wherein an imaging device in the plurality of imaging devices is configured to acquire infrared image data at a rate of at least approximately two thousand frames per second.

18. The system of claim 17, wherein the vehicle is one of: a road vehicle traveling up to at least approximately seventy miles per hour or a rail vehicle traveling up to at least approximately four hundred fifty kilometers per hour.

19. The system of claim 18, further comprising a computer system for evaluating the at least one vehicle component based on the image data, wherein the evaluating includes:
generating temperature measurement data based on the image data acquired by the plurality of imaging devices; and
evaluating the at least one vehicle component using the temperature measurement data.

20. The system of claim 19, wherein the evaluating determines a presence of at least one of a set of defects selected from: a hot brake, a cold brake, a hot wheel, or hot bearings.

* * * * *